(12) United States Patent
Dimauro (10) Patent No.: US 12,275,920 B2
(45) Date of Patent: Apr. 15, 2025

(54) COMPOSITIONS AND METHODS FOR CLARIFICATION OF BIOLOGICAL MATERIALS

(71) Applicant: Sunghee Lee Dimauro, Stamford, CT (US)

(72) Inventor: Sunghee Lee Dimauro, Stamford, CT (US)

(*) Notice: Subject to any disclaimer, the term of this patent is extended or adjusted under 35 U.S.C. 154(b) by 25 days.

(21) Appl. No.: 17/359,609

(22) Filed: Jun. 27, 2021

(65) Prior Publication Data

US 2021/0325282 A1    Oct. 21, 2021

Related U.S. Application Data

(60) Provisional application No. 63/045,171, filed on Jun. 28, 2020.

(51) Int. Cl.
| | | |
|---|---|---|
| *C11D 3/16* | (2006.01) | |
| *C11D 1/66* | (2006.01) | |
| *G01N 21/41* | (2006.01) | |
| *G01N 33/483* | (2006.01) | |

(52) U.S. Cl.
CPC ......... *C11D 3/168* (2013.01); *G01N 33/4833* (2013.01); *C11D 1/66* (2013.01); *G01N 21/41* (2013.01)

(58) Field of Classification Search
CPC .............................. C01G 41/00; B01J 27/188
See application file for complete search history.

(56) References Cited

U.S. PATENT DOCUMENTS

| | | | |
|---|---|---|---|
| 6,472,216 B1 | 10/2002 | Chiang | |
| 10,028,894 B2* | 7/2018 | Miller | A61K 6/30 |
| 2003/0191040 A1* | 10/2003 | Adriaanse | C11D 3/046 |
| | | | 510/530 |
| 2013/0045503 A1 | 2/2013 | Miyawaki et al. | |
| 2014/0087419 A1 | 3/2014 | Miyawaki et al. | |
| 2014/0178927 A1 | 6/2014 | Miyawaki et al. | |
| 2017/0227430 A1 | 8/2017 | Marini et al. | |
| 2017/0370810 A1 | 12/2017 | Miyawaki et al. | |
| 2018/0031452 A1 | 2/2018 | Imai et al. | |
| 2018/0180520 A1 | 6/2018 | Imai et al. | |
| 2019/0086302 A1 | 3/2019 | Ueda et al. | |
| 2020/0055884 A1* | 2/2020 | Daniels | C07F 11/005 |

FOREIGN PATENT DOCUMENTS

WO     2011111876 A1     9/2011

OTHER PUBLICATIONS

Staedler YM, Masson D, Schönenberger J (2013) Plant Tissues in 3D via X-Ray Tomography: Simple Contrasting Methods Allow High Resolution Imaging. Plos One 8(9): e75295. doi: 10.1371/journal.pone.0075295 (Year: 2013).*

(Continued)

*Primary Examiner* — Maris R Kessel
*Assistant Examiner* — Mickey Huang (57) ABSTRACT

The present disclosure relates to compositions and methods for clearing biological materials. Specifically, the present disclosure relates to increasing the transparency of biological materials via contact with clearing composition comprising a solution of polyoxometallate salt.

16 Claims, 4 Drawing Sheets

(56) References Cited

OTHER PUBLICATIONS

Sahiro et al., Preyssler-type phosphotungstate is a new family of negative-staining reagents for the TEM observation of viruses, 2022, Scientific reports, (2022) 12:7554 (Year: 2022).*

Ke, Meng-Tsen, et al. "SeeDB: a simple and morphology—preserving optical clearing agent for neuronal circuit reconstruction." Nature neuroscience 16, No. 8 (2013): 1154-1161.

Hama, Hiroshi, et al. "Sca le: a chemical approach for fluorescence imaging and reconstruction of transparent mouse brain." Nature neuroscience 14, No. 11 (2011): 1481-1488.

Chiang, Ann-Shyn, et al. "Insect NMDA receptors mediate juvenile hormone biosynthesis." Proceedings of the National Academy of Sciences 99, No. 1 (2002): 37-42.

Ertuck, Ali, et al. "Three-dimensional imaging of solvent-cleared organs using 3DISCO." Nature protocols 7, No. 11 (2012): 1983-1995.

Hanneman, W. William. "Sodium polytungstate as a gemmological tool." The Journal of Gemmology: 364. (1991).

Torresan, Michael E. The use of sodium polytungstate in heavy mineral separations. No. 87-590. US Geological Survey, 1987.

Hoover, Mark D. "Sodium metatungstate as a medium for measuring particle density using isopycnic density gradient ultracentrifugation." Journal of aerosol science 22, No. 2 (1991): 215-221.

Hou, Bing, et al. "Scalable and DiI-compatible optical clearance of the mammalian brain." Frontiers in neuroanatomy 9 (2015): 19.

Richardson, Douglas, et al. "Clarifying tissue clearing." Cell 162, No. 2 (2015): 246-257.

Tainaka, Kazuki, et al. "Chemical landscape for tissue clearing based on hydrophilic reagents." Cell reports 24, No. 8 (2018): 2196-2210.

\* cited by examiner

COMPOSITIONS AND METHODS FOR CLARIFICATION OF BIOLOGICAL MATERIALS

CROSS-REFERENCE TO RELATED CASES

This application claims benefit of earlier-filed, commonly-owned provisional application 63/045,171, filed 28 Jun. 2020, which is hereby incorporated by reference in its entirely.

GOVERNMENT DATA

This invention was made with government support under NSF grant NSF-CHE-1609135 awarded by the National Science Foundation. The government has certain rights in the invention.

FIELD

The present disclosure relates to compositions and methods for clearing biological materials. Specifically, the present disclosure relates to increasing the transparency of biological materials via contact with clearing composition comprising a solution of polyoxometallate salt.

BACKGROUND

Many biological materials, including, for example, organs or tissue, need to be observed microscopically. Such materials are ordinarily translucent, and as such, would have to cut into thin slices to allow for conventional 2D microscopy. Recently, three-dimensional (also sometimes referred to as "volumetric") microscopy has come to the fore, but in order to make this kind of microscopy more practical, enhanced methods of making biological material to be transparent have to be found. The origin of translucency in biological materials (such as tissue) is usually ascribed primarily (but not exclusively) to light scattering, which basically arises owing to differences in refractive index between the water content of the material (n=1.33) and the component of lipids and proteins of the materials (n usually greater than 1.44).

Real biological materials are complex, and are composed of cells, membranes, and organelles, and thus any visible light, when passing through the biological material, would be scattered in many directions. Since these varying components of biological materials may have differing refractive indices, light scattering will occur in many directions. If light scattering within the biological material is reduced, then an increase in light transmittance can usually be attained. The function of the clearance process is to ensure that scattering only happens in essentially one direction.

Developers have introduced many tissue clearing methods to improve the homogeneity of the refractive indices of biological materials, which renders the material more transmissive of light (usually, but not always, referring to visible light). The step of increasing the light-transmitting property of a biological material (such as a tissue) has been performed for a variety of reasons, such as improved visualization of gene expression taking place within a tissue, or intracellular localization, or visualization of cell morphology. This has usually been performed by a so-called clearing treatment, that increases the light-transmitting properties of the biological material. Tissue clearing methods generally allow for the study of the internal structure of the tissue, preferably with minimal tissue damage. Exemplary embodiments of biological tissues so studied, may include one or more of brain, liver, lungs, kidneys, intestines, heart, muscle, and blood vessels. For this process, many known clearing reagents and methods for treatment have been developed.

For example, one recent successful tissue clearing reagent is termed SeeDB. (M. T. Ke et al., Nat. Neurosci. 16(8): 1154-1161 (2013). The SeeDB method performs washes of biological tissue in solutions of fructose with 1-thioglycerol. The SeeDB reagent, in its most concentrated form, has a high refractive index, n=1.51, matching the RI of most oil immersion objectives on microscopes. The tissue can be cleared in several days, while retaining any fluorescent signal present in the tissue. Some limitations of SeeDB include its reported inability to allow for antibody staining, and suffering from an increased browning of the tissue.

Other important methods for tissue clearing include Scale (H. Hama, Nat. Neurosci. 14(11):1481-1490 (2011) and WO2011/111876) and FocusClear (A. S. Chiang et al., Proc. Natl. Acad. Sci. 99(1):37-42 (2002) and U.S. Pat. No. 6,472,216) or 3DISCO (A. ErtUrk et al., Nat. Protoc. 7(11):1983-1995 (2012)). The following US patent publications are also representative of important recent tissue clearing methods and compositions, and all of the following US patent publications are hereby incorporated by reference in their entirety, especially for purposes of providing written description of additional tissue clearing protocols and methods: US-2014/178927; US-2017/227430; US-2017/370810; US-2018/031452; US-2019/086302; US-2018/180520; US-2014/087419; and US-2013/045503.

Despite the numerous methods and compositions for tissue clearing, including aqueous and nonaqueous ones, there are numerous disadvantages for many of those tissue clearing compositions of the prior art. For example, many nonaqueous tissue clearing compositions comprise organic compounds that may have toxic effects. For many aqueous tissue clearing compositions, these are usually slow in permeating into biological materials, or may have an overly high osmotic pressure, thereby dehydrating biological materials to an undue extent. There remains a need for new aqueous-based tissue clearing compositions which overcome some or all of the above-noted disadvantages.

BRIEF DESCRIPTION OF THE INVENTION

In a first aspect of the disclosure is provided a clearing composition for increasing the transparency of a biological material, the clearing composition comprising an aqueous solution of a polyoxometallate salt and optionally a surfactant or detergent, the clearing composition comprising a refractive index of greater than about 1.40 at a visible light wavelength.

In a second aspect of the disclosure is provided a method for a clearing treatment for increasing the transparency of a biological material, the method comprising: permeating, into an isolated biological material, a clearing composition comprising an aqueous solution of a polyoxometallate salt and optionally a surfactant or detergent, the clearing composition comprising a refractive index of greater than about 1.40 at a visible light wavelength, the clearing composition permeating into the biological material so that the biological material is increased in transparency.

In a third aspect of the disclosure is provided a system for a clearing treatment for increasing the transparency of a biological material, the system comprising: a clearing composition comprising an aqueous solution of a polyoxometallate salt and optionally a surfactant or detergent, the clearing composition comprising a refractive index of greater than about 1.40 at a visible light wavelength; and a biological material which has been isolated; wherein the clearing composition having permeated into the biological material so that the biological material is increased in transparency or light-transmittance.

In a fourth aspect of the disclosure is provided a method for preparing a biological material with increased light-transmitting properties, the method comprising: a permeating step comprising contacting the biological material with a clearing composition comprising an aqueous solution of a polyoxometallate salt and optionally a surfactant or detergent, the clearing composition comprising a refractive index of greater than about 1.40 at a visible light wavelength, to permeate the clearing composition into the biological material and increasing the light transmitting properties of the biological material; wherein the light-transmitting property comprises a light transmitting property in which a proportion of transmitted light, with respect to incident light, is 40% or more.

In a fifth aspect of the disclosure is provided an immunohistochemical or biochemical assay being characterized by using a biological material prepared by a method comprising: permeating into an isolated biological material a clearing composition comprising an aqueous solution of a polyoxometallate salt and optionally a surfactant or detergent, the clearing composition comprising a refractive index of greater than about 1.40 at a visible light wavelength, the clearing composition permeating into the biological material so that the biological material is increased in transparency.

DETAILED DESCRIPTION

As would be understood by the person having ordinary skill in the art, a polyoxometallate (sometimes written as "polyoxometalate") is a polyatomic anion that comprises three or more transition metal oxyanions linked together by shared oxygen atoms to form a substantially-closed three-dimensional framework. The metal transition atoms may typically be one or more of Group 6 (Mo, W) or Group 5 (V, Nb, Ta) transition metals. Generally, at least two families of polyoxometallate are recognized, including the isopolymetallates (where the metal complex is comprised of only one kind of transition metal, as well as oxygen), and the heteropolymetallates, comprised of one transition metal, oxygen, and a main group oxyanion (such as phosphate, silicate, or the like). For example, there is the well known families of silicon-containing heteropolymetallates (e.g., the alkali metal salts of silicotungstate) and phosphorus-containing heteropolymetallates (e.g., the alkali metal salts of phosphotungstate). A specific embodiment of polyoxometallate salt may include an alkali metal salt of metatungstate.

The term "light-transmitting", as used herein, generally may refer to either (i) the proportion of light transmitted through a biological material, relative to incident light or (ii) the extent to which fluorescence (as induced by a source of excitation) passes through and/or escapes from a biological material. Light transmittance (T) may be expressed as the percent of incident light which is transmitted. By way of example, a completely opaque substance is considered to have 0% T, but pure water has 100% T. In the present disclosure, it is possible to achieve a transmittance for a biological material of 40% or more, often 50% or more, 60% or more, 70% or more, 80% or more, 90% or more, 95% or more, 98% or more, or 99% or more.

In accordance with the present disclosure, the term "biological material" is not particularly limited. A biological material may be derived from a plant or an animal, such as animal such as fish, amphibian, reptile, bird, or mammal. In most instances, a biological material is derived from a mammal such as mouse, rat, rabbit, guinea pigs, non-human primates, canine, cat, cattle, horse, or human. A biological material may be an organ, tissue, bodily fluid, or cell excised from an animal. In some embodiments, the biological material may be a tissue specimen including a fluorescent material contained therein; or a biological tissue stained with a fluorescent material; or a biological tissue comprising a fluorescent protein-expressing cell therein.

The embodiments of the present disclosure can significantly improve the light-transmitting property of a biological material, and can thus be combined with modern microscopic techniques to allow enhanced tissue imaging. It is an aim of the present disclosure to minimize quenching of signals of a fluorescent label, or make a biological transparent enough to be observed by a light-sheet microscope.

In accordance with embodiments of this disclosure, the permeating step comprising contacting the biological material with the clearing composition, may be performed at any suitable temperature which is not particularly limited. For example, the temperature may be in a range of 15° C. (or more) up to 45° C. (or less). The total processing time for the permeating step comprising contacting the biological material with the clearing composition, may be any effective time, for example, in a range of 2 hours or more to 120 hours or less. A pressure at which the permeating step is performed is not particularly limited.

The clearing composition is hereinbelow described, in various embodiments. As previously mentioned, in a first aspect of the disclosure is provided a clearing composition for increasing the transparency of a biological material, the clearing composition comprising an aqueous solution of a polyoxometallate salt, the clearing composition comprising a refractive index of greater than about 1.40 at a visible light wavelength. Typically, the visible light wavelength at which the refractive index may be measured, is in a yellow light wavelength such as sodium vapor emission wavelength (589 nm). Usually, the clearing composition may exhibit a refractive index of greater than about 1.40 when measured at 298 K at such visible light wavelength. In various embodiments, the clearing composition of the present disclosure may comprise a refractive index in a range of from about 1.41 to about 1.55 (such as greater than about 1.45, such as from 1.46 to 1.55; or such as greater than about 1.47, such as 1.48, 1.49. 1.50, or 1.51). If the refractive index is too low, then the ability of the clearing composition to reduce scattering in the biological material into which it is permeated, is reduced. If the refractive index is too high, then the clearing composition comprising polyoxometalate may exhibit an unduly high viscosity (since refractive index and concentration of solute, and thus resultant viscosity, are positively related), slowing down its permeation into a biological material.

In certain embodiments, the clearing composition of the present disclosure may comprise a viscosity of about 50 mPa-s or less (when measured at 298 K), such as about 40 mPa-s or less, or about 30 mPa-s or less. Particular ranges may include, a range from about 1 mPa-s to about 30 mPa-s, or more narrowly, from about 5 mPa-s to about 20 mPa-s.

A clearing composition of the present disclosure, in use, may act to increase the transparency of a tissue or an organ derived from a multicellular animal; or may act to increase the transparency of a multicellular animal which is not a human. As used herein, the phrase "increasing the transparency of the biological material" may comprise, preparing a biological material having increased light-transmitting property.

The osmotic pressure of a solution may typically be measured as osmolality (mOsm/kg). Thus, in various embodiments, the clearing composition may comprise an osmolality of about 3000 mOsm/kg or less when measured at 298 K (such as an osmolality in a range from about 100 mOsm/kg to about 3000 mOsm/kg, e.g., from about 1500 mOsm/kg to about 3000 mOsm/kg). If the osmolality is too low, then the polyoxometalate salt may not be able to perform its function of increasing transparency of a biological material. If osmolality of the clearing composition is too high, then the biological material into which the clearing composition is permeated, may suffer from an undesirable extent of shrinkage due to osmotic dehydration.

Aqueous solutions of some polyoxometallate salts are characterized by the ability to form solutions of high specific gravity (i.e., density) as compared to water. The clearing composition of the present disclosure may typically comprise a density of about 2.5 g/mL or less at 25° C., such as from about 1.5 g/mL to about 2.5 g/mL.

The concentration of polyoxometallate salt in the clearing composition is not particularly limited, provided that the clearing composition comprises a refractive index of greater than about 1.40 at a visible light wavelength. However, in order to confer a high refractive index to the composition while avoiding unduly high viscosity, the clearing composition may comprise the polyoxometallate salt at a mass fraction of from about 0.20 to about 0.80, such as from about 0.3 to about 0.7. In such cases, the complement will comprise at least water, as well as any other added components. In some embodiments, the clearing composition may comprise the polyoxometallate salt (measured as anhydrous) in an amount of at least about 50 wt %, such as from about 51 wt % to about 99 wt %.

In various embodiments, the clearing composition may further comprise at least one surface-active agent or surfactant or detergent as an added component. A surfactant may be included in order to promote the delipidation of the biological material and/or to promote penetration of substances into the biological material. In some embodiments, a surfactant may comprise a nonionic surfactant, such as a Triton-X or a Tween surfactant or NP-40 or saponin; or the like. In other embodiments, the surfactant may comprise an anionic (e.g., sodium dodecyl sulfate), or cationic, or catanionic surfactant.

In some embodiments, the clearing composition of the present disclosure may comprise, as an added component, an alcohol (such as a mono-alcohol (e.g., methanol or ethanol) or a dialcohol (e.g., a glycol) or a trialcohol (e.g., glycerol or glycerin), or a non-ionic organoiodine compound. In accordance with certain embodiments, the clearing composition may comprise, as added components, one or more of a water soluble organic compound selected from one or more of saccharide (e.g., monosaccharide or disaccharide), ether, ester, or ketone. For example, sucrose or fructose may be present to increase refractive index. In accordance with yet further embodiments of the present disclosure, the clearing composition may further comprise at least one compound selected from the group consisting of urea and a urea derivative. The latter may advantageously function to increase hydration ability and promote penetrance of water and materials into the tissue.

As would be well understood by persons skilled in the relevant fields, polyoxometallate salts may be provided in various chemical forms, including as a isopolyoxometallate salt or a heteropolyoxometallate salt. Isopolyoxometallate salt refers to a type of polyoxometalate salt having only one kind of transition metal element in the anionic moiety. Heteropolyoxometalate salt comprises at least two kinds of metal element or metalloid element in the anionic moiety. Examples of a heteropolyoxometalate salt include sodium silicotungstate, wherein the anionic moiety comprises the tungsten (a transition metal) and silicon (a metalloid element). Another example of a heteropolyoxometalate salt is an alkali metal salt of phosphotungstic acid. A heteropolyoxotungstate salt is formally a salt of a heteropolytungstic acid, having (as its cationic moiety) one or more of (for example), an alkali metal, or $NH_4^+$, or quaternary ammonium ion.

In some embodiments, the clearing composition may comprise an isopolyoxometallate salt. An example of an isopolyoxometallate salt may be sodium metatungstate (e.g., $Na_6H_2W_{12}O_{40} \cdot xH_2O$, where x is from 1 to 3). Another example of an isopolyoxometallate salt may be lithium metatungstate (e.g., $Li_6H_2W_{12}O_{40} \cdot xH_2O$ where x is from 1 to 3).

A clearing composition in accordance with embodiments of the present disclosure is a solution, typically a homogeneous or substantially homogeneous solution. Such solution comprises a solvent in which polyoxometallate salt is soluble. The solvent is not limited to any particular kind, provided that polyoxometallate salt is soluble in the solvent. Preferably, water is used as a main solvent, meaning, a majority of the solvent (by volume) in the solution, is $H_2O$. In certain embodiments, the solvent consists of water or consists essentially of water. Note that, in an embodiment of the present invention, what is meant by the expression "water is used as a main solvent" is that water is used in an amount which accounts for more than 50% (and 100% or less) of a total volume of all solvents used. In some embodiments, other components other than water may be present as part of the solvent in the solution. Examples of such other components are, dimethyl sulfoxide (DMSO) or ethanol or methanol or other alcohol solvent; or the like.

As noted, aspects of the present disclosure provide a method for a clearing treatment for increasing the transparency of a biological material, the method comprising permeating, into an isolated biological material, a clearing composition comprising an aqueous solution of a polyoxometallate salt, the clearing composition comprising a refractive index of greater than about 1.40 at a visible light wavelength, the clearing composition permeating into the biological material so that the biological material is increased in transparency.

In another aspect of the disclosure is provided a method for preparing a biological material with increased light-transmitting properties, the method comprising: a permeating step comprising contacting the biological material with a clearing composition comprising an aqueous solution of a polyoxometallate salt, the clearing composition comprising a refractive index of greater than about 1.40 at a visible light wavelength, to permeate the clearing composition into the biological material and increasing the light transmitting properties of the biological material; wherein the light-transmitting property comprises a light transmitting property in which a proportion of transmitted light, with respect to incident light, is 40% or more.

The step of contacting a biological material with the clearing composition can be performed in sequential stages, even using different kinds of clearing compositions, including the clearing composition of the present disclosure. For example, contacting of the biological material with the instant clearing composition may be performed in two or more stages. In some embodiments, the concentrations of polyoxometallate salt are increasingly higher (in the clearing composition) as the number of stages progresses. This is because, in such a case, solution of polyoxometallate salt may more efficiently permeate into a biological material.

One or more additional steps may be performed before and/or after the step of permeating the polyoxometallate composition in the biological material. These steps may include one or more of the following: (i) a treatment step in which pigment molecules are removed from the biological material; (ii) a permeabilization step which may improve diffusion of other materials (including, e.g., the instant polyoxometallate salt solution) into a biological material, such as by contact with a detergent; (iii) an immunolabeling step in which a fluorescent probe may be affixed to molecules (e.g., proteins) in the biological material. For example, all of these steps (i)-(iii) may be performed prior to the step of permeating the polyoxometallate salt composition in the biological material, or a subset of these steps may be performed, or none at all.

Once a biological material has been subjected to permeation with the clearing composition of the present disclosure, typically an observation step using (for example) an optical microscope is performed. Some further treatment steps, such as staining or marking, may also need to be performed on the biological material. Such further treatment steps may be performed (i) before the permeation with the instant clearing composition, and/or (ii) after the permeation with the instant clearing composition and before the observation step. For example, in a case where further treatment involves use of a fluorescent protein, a fluorescent protein gene is introduced into a living biological material before the clearing composition so that the fluorescent protein will be expressed therein. In a case where the further treatment step is (i) injection of luminescent compound into a biological material or (ii) staining of a biological material with luminescent compound, the further treatment step may be performed before (or during) a step of treatment with the instant clearing composition. However, the further treatment step may be performed after the clearing treatment step. Alternatively, the further treatment step may be performed by staining of a biological material with a non-luminescent compound.

The observation step may be done with the assistance of an optical microscope, e.g., a 3D super-resolution microscope technique such as STED, 3D PALM, FPALM, 3D STORM, or SIM. Also, it is possible for observation step being performed by use of a multiphoton excitation technique. Alternatively, microscopic observation may be done with a single-photon confocal microscope or light-sheet microscope.

EXAMPLES

This set of Examples is intended to demonstrate the effectiveness with which the disclosed clearing composition can increase the transparency of a model lipid bilayer or of real biological tissue. Lipid bilayers are a major component of cell membranes, and contribute greatly to the light scattering that causes the translucency or opacity of biological materials.

The salt sodium metatungstate (also known as sodium polytungstate or SPT), was provided. Its formula was $Na_6[H_2W_{12}O_{40}]$, alternatively formulated as $3Na_2WO_4 \cdot 9WO_3 \cdot H_2O$. It is a white powder, water soluble, with low toxicity.

An aqueous solution of SPT at a nominal concentration of 57 wt % was prepared. The units of weight percent indicate that, effectively, 57 g of SPT is dissolved into 43 g of water. Specifically, 1 mL of solution of made by weighing 1.32447 g of SPT powder into a tared Eppendorf container. Then, 1.00403 g of 18-megaohm distilled water was added until the total mass of the mixture is 2.3285 g. The Eppendorf container was gently vortexed at room temperature until dissolved. The density of the resultant aqueous solution was 1.855 g/mL and refractive index was 1.4395, measured by Abbe refractometer under light from sodium-vapor-lamp. Osmolality was measured with vapor-phase osmometer at room temperature (Vapro) and found to be 1498 mOsm/kg.

A glass chamber formed from two parallel pyrex plates, previously hydrophobized by exposure to hexamethyldisilazane. The chamber was filled with an 14 mM oil solution of glyceryl-1-monooleate (GMO) in squalane ($C_{30}H_{62}$).

Control Example 1

Figure 1:
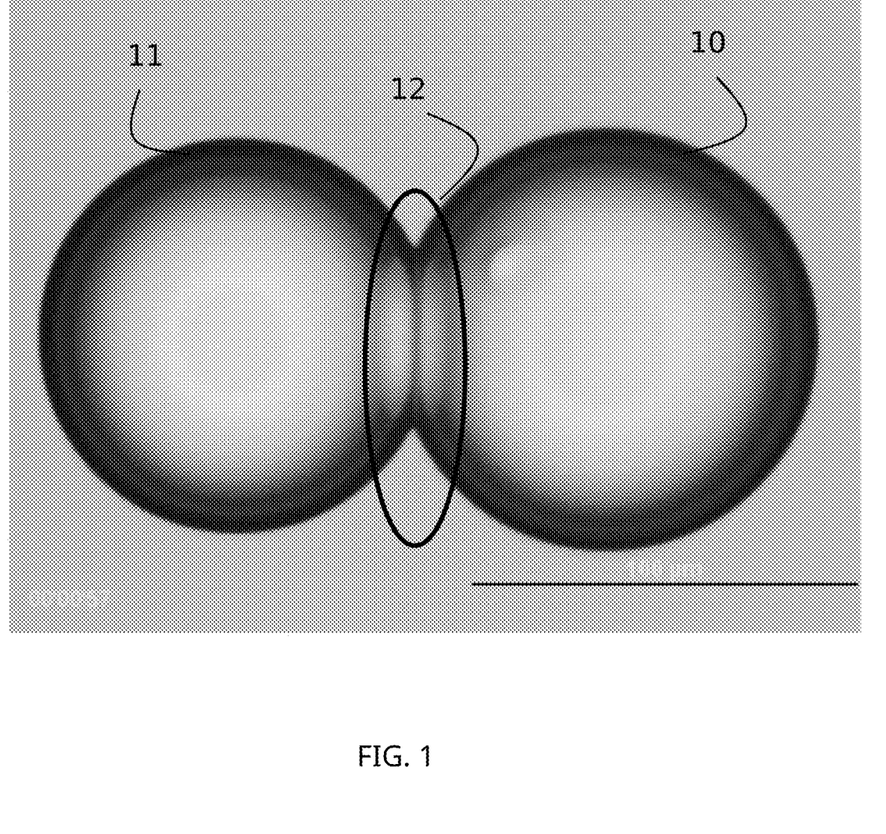
FIG. 1 depicts a photomicrograph of a model lipid bilayers in the absence of a clearing composition.

Into the chamber was introduced two isolated droplets of pure (18 MΩ) water, each of which was about 100 micrometers in diameter. Glass micropipets were used to dispense the droplets. The two droplets were incubated in the solution of GMO lipid for several minutes, and then urged to contact each other, forming a droplet interface bilayer (DIB). In FIG. 1 is shown a photomicrograph of the two pure water droplets (10, 11) in contact with each other, taken with a camera on an inverted phase-contrast microscope. The region of contact (12) between the two droplets is an side-view of a self-assembled droplet bilayer composed of GMO lipid. Since a bilayer of GMO lipid has a refractive index (RI) of about 1.43, and the refractive index of pure water is about 1.33, the contact region 12 (i.e., GMO droplet lipid bilayer) appears dark under phase contrast microscopy, owing to the RI difference.

Experimental Example 1

Figure 2:
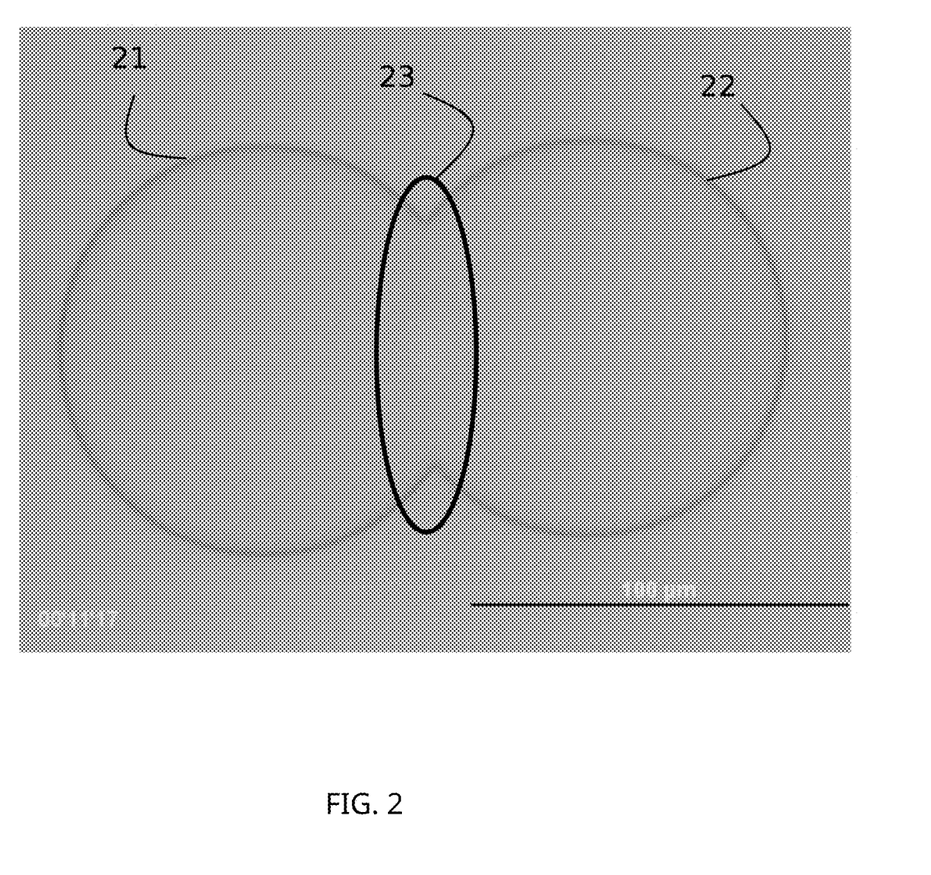
FIG. 2 depicts a photomicrograph of a model lipid bilayer in the presence of embodiments of the described clearing compositions.

Separately, two aqueous microdroplets (21, 22), each of which had diameter of about 100 micrometer, composed of the above SPT solution, were dispensed into the chamber of GMO (14 mM) in squalane. Again, the droplets (21, 22) were incubated as above, and then urged into contact, to form a DIB at their interdroplet contact zone (23). In FIG. 2 is shown a photomicrograph of the two SPT droplets in contact with each other, taken with a camera on an inverted phase-contrast microscope. The region of contact (23) between the two droplets is now invisible to phase-contrast microscopy. Since a bilayer of GMO lipid has a refractive index (RI) of about 1.43, and the refractive index of SPT used in this example is 1.4395, then the contact region (23) between the two droplets cannot be visualized under phase contrast microscopy, owing to the fact that essentially no difference in refractive index exists between the clearing composition comprising polyoxometallate salt solution, and the lipid bilayer. This is significant for the process of tissue clearing for the following reason. Biological tissue, especially tissue of mammalian organisms, is composed of cells that are bounded (defined) by a surrounding cell membrane with the structure of a lipid bilayer. Since the lipid bilayer which exists at contact region 23 is similar in nanoscopic size and composition and structure as the bilayer which exists in cell membranes, and since the clearing composition of Experimental Example 1 is capable of fully transparentizing this biomimetic bilayer, this is indicative of the power of the disclosed clearing compositions in performing their inventive function.

Experimental Example 2

Liposomal suspensions were prepared by dispersing DPPC lipid in either pure water, or in an exemplary embodiment of the present clearing composition. DPPC is a phospholipid (more specifically, a phosphatidylcholine lipid) with two hydrocarbon tailgroups of sixteen carbons each (palmitoyl groups). When dispersed in aqueous suspension, it is well known to form small unilamellar vesicles (liposomes) of diameter in the range of from (e.g.,) about 50 to 200 nm, depending upon the energy input during the dispersion process (e.g., vortexing or sonication) and depending upon the process used to extrude and filter the suspension. In each case (i.e., in the case of the dispersing in pure water, and in the case of the dispersing in exemplary clearing composition), DPPC lipid was suspended in aqueous solution at a concentration of 3.9 mg/mL.

Figure 3:
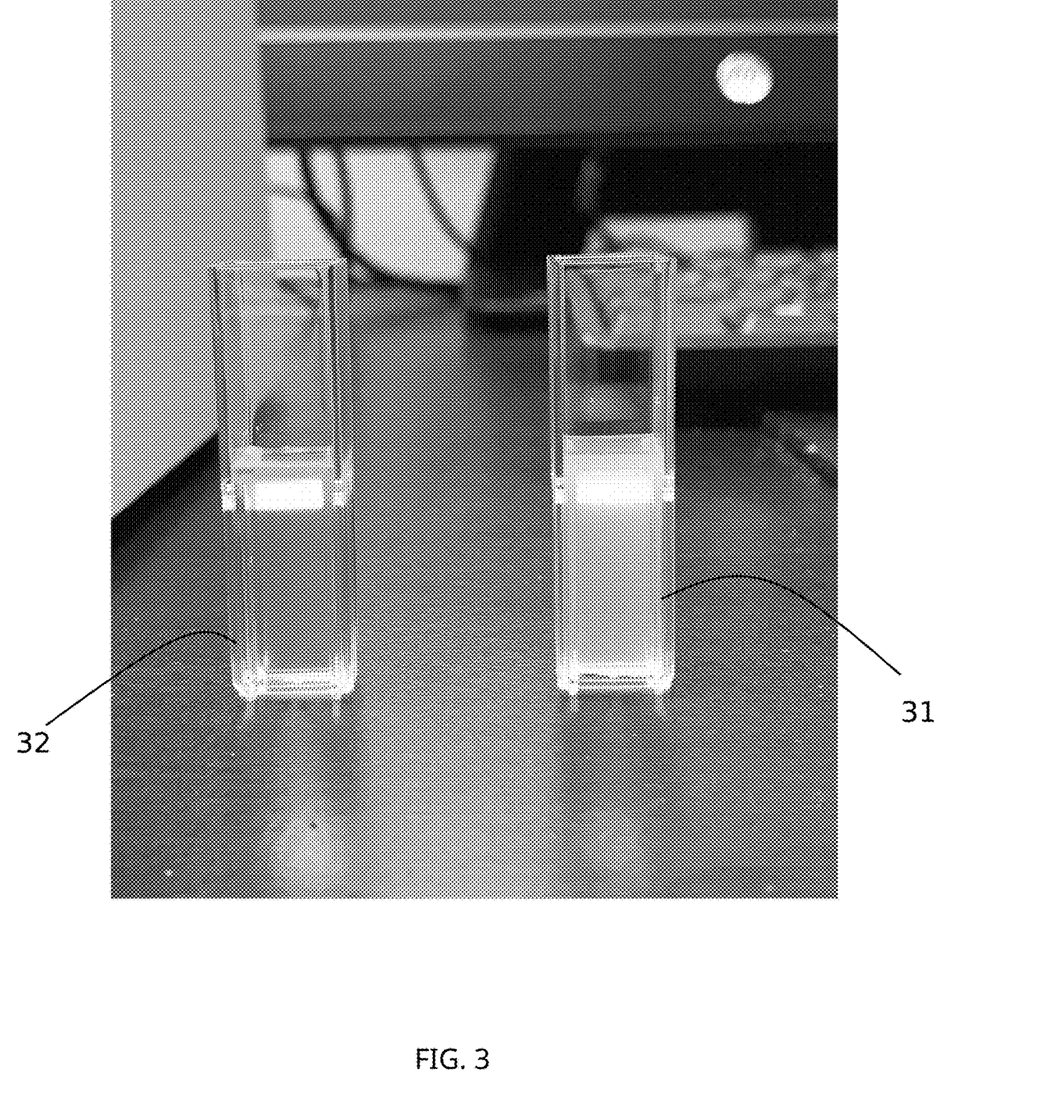
FIG. 3 is a photograph of samples of a DPPC liposomal suspension in the presence and absence of embodiments of the described clearing compositions.

In a first example, DPPC lipid was suspended in pure water (refractive index 1.334) to form "DPPC-water liposomal suspension". In a second example, DPPC lipid was suspended in an aqueous solution of sodium metatungstate (SPT) at a 65% wt/wt SPT, prepared by dissolving 0.65 mg SPT into 0.35 mg $H_2O$; the SPT solution, prior to addition of lipid, had refractive index of 1.466. The result of the latter, second example is "DPPC-SPT liposomal suspension". Each suspension was (separately) vortexed for a period of about 2 min, and then sonicated for 30 minutes at 40 degrees C. After sonication, each suspension was placed into a cuvette with 1 cm path-length. In FIG. 3 is seen a photograph of two cuvettes (31, 32), each of which is a hollow quartz cuvette of rectangular prism shape, of width 1 cm. Cuvette 31 contains DPPC-water liposomal suspension, and cuvette 32 contains DPPC-SPT liposomal suspension. The photograph of FIG. 3 shows that the dispersion in pure water (31) is cloudy when observed visually under ordinary room light, whilst the dispersion in SPT (32) is almost completely clear. The pure-water suspension in cuvette 31 had an transmittance of 0.438 at 600 nm incident light. The SPT suspension in cuvette 32 had transmittance value of 0.798 at 600 nm. The use of the SPT aqueous solution increased the transmittance of the DPPC liposomal suspension by 45%. Ordinarily, liposomal suspensions of DPPC in pure water appear to have relatively low light transmittance due to the light scattering caused by the refractive index mismatch between the RI of the water (1.334) and the RI of the DPPC bilayer (1.475). The use of an exemplary clearing composition was observed to significantly increase the transmittance of visible light through a model bilayer membrane: a biomimetic model of the cell membrane found in the cellular components of biological tissue.

Experimental Example 3

Figure 4:
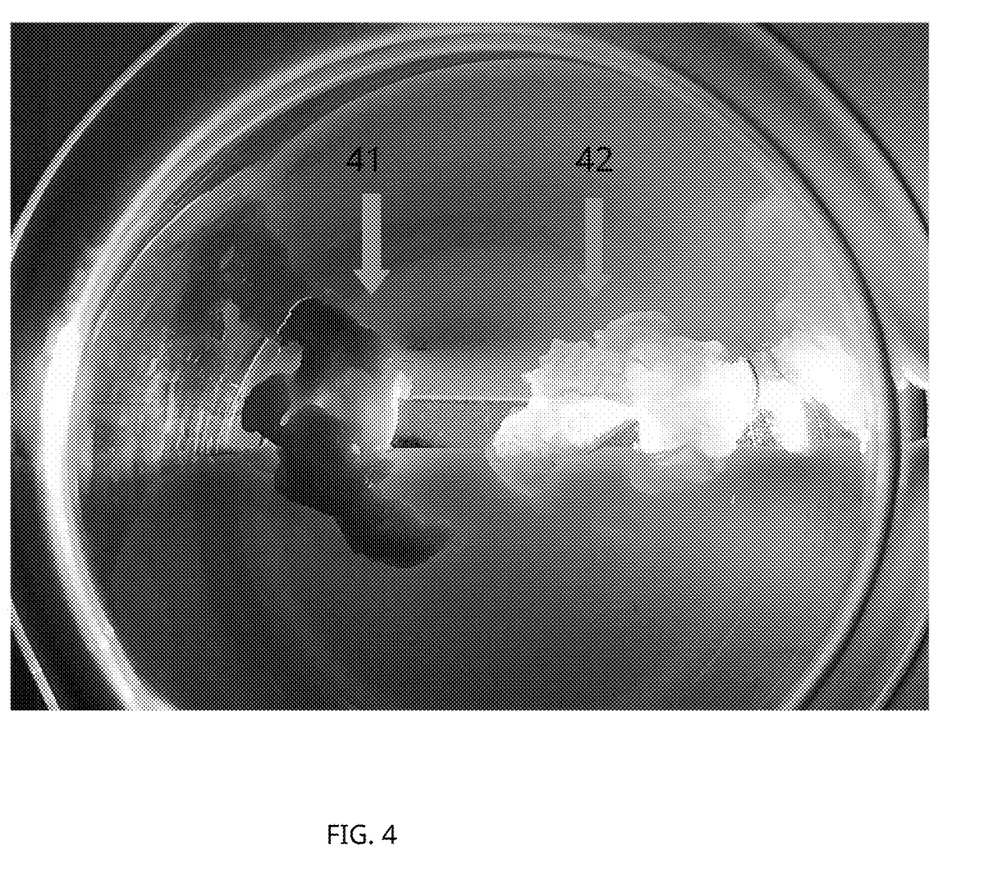
FIG. 4 depicts the tissue-clearing effect of embodiments of the described clearing compositions upon muscle tissue after simple immersion.

An aqueous solution of SPT at a nominal concentration of 57 wt % was prepared. The density of the resultant aqueous solution was 1.855 g/mL and refractive index was 1.4395. Two samples of raw smooth muscle tissue excised from *Gallus domesticus* were provided. Each sample was about 1 cm thick. A first sample was immersed in distilled conductivity water for 24 h at 298 K, and a second sample was immersed in the 57 wt % solution of SPT for 24 h at 298 K. In FIG. 4 is seen the result. Both samples were removed from their respective solutions and placed in a petri dish. A high-power white LED light source was placed below the petri dish to compare the level of transmitted light. Sample 41 of FIG. 4 was the first sample that had been immersed solely in distilled conductivity water; and sample 42 was the second sample, treated with an exemplary clearing composition by simple immersion. It was observed that sample 42 exhibited a markedly greater level of transmission of the visible light, at comparable tissue thicknesses, without any noticeable discoloration, shrinkage, expansion, or loss of tissue cohesiveness.

By homogenizing refractive indices of the biological tissue components, scattering of tissue-penetrating light is reduced, which would otherwise cause such problems as image distortion, resolution decrease during imaging process due to laser light scattering, and imaging depth decrease resulting from laser transmission decrease.

Unlike many organic-solvent based clearing compositions, aqueous solutions of high refractive index such the instant aqueous polyoxometallate salt solutions may provide an environment that is more friendly to proteins, and does not adversely interfere with fluorophores that are present and/or introduced to the biological material. For example, aqueous sodium metatungstate solutions (an exemplary embodiment of an aqueous polyoxometallate salt solution), are colorless and would not interfere with the emission of a fluorophore; and, absorption first begins in the UV region at about 320 nm, increases dramatically at wavelengths below 290 nm and reaches a maximum at 257 nm. And, while RIs of up to about 1.48 can be attained by using sugar solutions at very high concentration (e.g., sucrose, fructose, or the like), such sugar solutions typically exhibit an adverse high viscosity, often akin to that of honey. For example, the prior art clearing composition known as FRUIT (which is a solution of fructose and urea), at "100%" concentration level, has an RI of 1.48 (at 18° C.) and a viscosity of (at 29° C.) of about 450 mPa-s. In contrast, typical aqueous polyoxometallate salt solutions of even higher refractive index (e.g., n=1.50) may have typical viscosity (at 25° C.) of less than about 10 mPa-s. This can speed infiltration and/or impregnation and/or permeation of the instant composition into the biological material, for more rapid clearing. Furthermore, without being limited by theory, the anionic nature of polyoxometallate salt solutions may be advantageous, in that such anionic salt would not likely interact with anionic cell membranes (lipid bilayers), as readily as other aqueous clearing compositions.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described. It is to be understood that the foregoing description is intended to illustrate and not to limit the scope of the invention, which is defined by the scope of the appended claims. Other embodiments are within the scope of the following claims.

I claim:

1. A method for a clearing treatment for increasing the transparency of a biological material, the method comprising: permeating, into an isolated biological material, a clearing composition comprising an aqueous solution of a polyoxometallate salt present in an amount of at least about 50 wt % and at least one component selected from the group consisting of mono-alcohol, dialcohol, trialcohol, monosaccharide, disaccharide, urea, and non-ionic organoiodine compound, the clearing composition comprising a refractive index of greater than about 1.40 at a visible light wavelength, the clearing composition permeating into the isolated biological material so that the isolated biological material is increased in transparency,
   wherein the isolated biological material comprises tissue or organ derived from a multicellular animal; and
   after permeating, performing an observation step of the isolated biological material with an optical microscopy technique.

2. The method of claim 1, wherein the optical microscopy technique is a super-resolution microscopy technique.

3. The method of claim 2, wherein the super-resolution microscopy technique is selected from STED, 3D PALM, FPALM, 3D STORM, or SIM.

4. The method of claim 1, where the polyoxometallate salt comprises a transition metal selected from one or more of Mo, W, V, Nb, and Ta.

5. The method of claim 1, wherein the polyoxometallate salt is an isopolyoxometallate salt or a heteropolyoxometallate salt.

6. The method of claim 1, wherein the polyoxometallate salt is an isopolyoxotungstate salt selected from the group consisting of metatungstate salt and polytungstate salt.

7. The method of claim 1, wherein the clearing composition comprises a refractive index in a range of from about 1.46 to about 1.55.

8. The method of claim 1, wherein the clearing composition further comprises at least one surfactant or detergent.

9. A method for a clearing treatment for increasing the transparency of a biological material, the method comprising:
   permeating, into an isolated biological material, a clearing composition comprising an aqueous solution of a polyoxometallate salt present in an amount of at least about 50 wt %, the clearing composition comprising a refractive index of greater than about 1.40 at a visible light wavelength, the clearing composition permeating into the isolated biological material so that the isolated biological material is increased in transparency,
   wherein the isolated biological material comprises tissue or organ derived from a multicellular animal; and
   after permeating, performing an observation step of the isolated biological material with an optical microscopy technique.

10. The method of claim 9, wherein the clearing composition further comprises at least one component selected from the group consisting of mono-alcohol, dialcohol, trialcohol, ether, ester, ketone, monosaccharide, disaccharide, urea, and non-ionic organoiodine compound.

11. The method of claim 9, wherein the clearing composition further comprises at least one surfactant or detergent.

12. The method of claim 9, wherein the optical microscopy technique is a super-resolution microscopy technique.

13. The method of claim 9, where the polyoxometallate salt comprises a transition metal selected from one or more of Mo, W, V, Nb, and Ta.

14. The method of claim 9, wherein the polyoxometallate salt is an isopolyoxometallate salt or a heteropolyoxometallate salt.

15. The method of claim 9, wherein the polyoxometallate salt is an isopolyoxotungstate salt selected from the group consisting of metatungstate salt and polytungstate salt.

16. The method of claim 9, wherein the clearing composition comprises a refractive index in a range of from about 1.46 to about 1.55.

* * * * *